US008042543B2

(12) United States Patent
Amarasinghe et al.

(10) Patent No.: US 8,042,543 B2
(45) Date of Patent: *Oct. 25, 2011

(54) HEADGEAR ASSEMBLY FOR A RESPIRATORY MASK ASSEMBLY

(75) Inventors: Amal S. Amarasinghe, West Pennant Hills (AU); Perry D. Lithgow, Moruya (AU); Memduh Guney, Killara (AU)

(73) Assignee: ResMed Limited, Bella Vista (AU)

( * ) Notice: Subject to any disclaimer, the term of this patent is extended or adjusted under 35 U.S.C. 154(b) by 260 days.

This patent is subject to a terminal disclaimer.

(21) Appl. No.: 12/285,445

(22) Filed: Oct. 6, 2008

(65) Prior Publication Data
US 2009/0038622 A1  Feb. 12, 2009

Related U.S. Application Data

(63) Continuation of application No. 10/655,602, filed on Sep. 5, 2003, now Pat. No. 7,509,958.

(60) Provisional application No. 60/424,694, filed on Nov. 8, 2002.

(51) Int. Cl.
*A62B 18/08* (2006.01)
*A62B 17/04* (2006.01)
*A62B 18/02* (2006.01)
*A61M 16/00* (2006.01)

(52) U.S. Cl. ......... 128/207.11; 128/206.24; 128/206.26; 128/206.27; 128/206.28; 128/207.13; 128/207.17; 128/201.22; 128/201.23; 128/201.19; 128/205.25; 2/9; 2/173; 24/71.1

(58) Field of Classification Search ............. 128/206.24, 128/206.26, 206.27, 206.28, 207.11, 207.13, 128/207.17, 201.22, 201.23, 201.19, 205.25; 2/9, 173; 24/71.1, 68 SK, 68 E, 194, 196, 24/484, 591.1, 593.11, DIG. 43, DIG. 47
See application file for complete search history.

(56) References Cited

U.S. PATENT DOCUMENTS

RE20,211 E   12/1936  Motsinger
2,353,643 A   7/1944  Bulbulian
(Continued)

FOREIGN PATENT DOCUMENTS
JP   2002-537078   11/2002
(Continued)

OTHER PUBLICATIONS

Japanese Office Action and English translation for copending Japanese Application No. 2004-548920, mailed Mar. 16, 2010, 8 pages.
(Continued)

*Primary Examiner* — Patricia Bianco
*Assistant Examiner* — Nihir Patel
(74) *Attorney, Agent, or Firm* — Nixon & Vanderhye P.C.

(57) ABSTRACT

A respiratory mask assembly for delivering breathable gas to a patient includes a frame and a headgear assembly removably attachable to the frame. The headgear assembly includes a pair of side portions and a rear portion that interconnects the pair of side portions. The pair of side portions includes at least one strap. The rear portion has at least one strap constructed of at least two layers of material. One of the layers of material has a more rigid construction than the other of the layers of material to resist compression of the at least one strap of the rear portion in a first direction which resists movement of the at least one strap of the pair of side straps in the first direction.

31 Claims, 16 Drawing Sheets

U.S. PATENT DOCUMENTS

| | | | |
|---|---|---|---|
| 4,593,688 A | 6/1986 | Payton | |
| 5,233,978 A | 8/1993 | Callaway | |
| 5,771,886 A | 6/1998 | Maire et al. | |
| 6,338,342 B1 | 1/2002 | Fecteau et al. | |
| 6,374,826 B1 | 4/2002 | Gunaratnam et al. | |
| 6,422,238 B1 | 7/2002 | Lithgow | |
| 6,467,483 B1 | 10/2002 | Kopacko et al. | |
| 7,509,958 B2 * | 3/2009 | Amarasinghe et al. | 128/206.24 |
| 2002/0117177 A1 | 8/2002 | Kwok | |
| 2003/0196657 A1 | 10/2003 | Ging et al. | |
| 2004/0112377 A1 | 6/2004 | Amarasinghe et al. | |

FOREIGN PATENT DOCUMENTS

| | | |
|---|---|---|
| WO | WO 97/20597 | 6/1997 |
| WO | WO 00/50122 | 8/2000 |
| WO | WO 02/07806 A1 | 1/2002 |
| WO | WO 02/47749 A1 | 6/2002 |
| WO | WO 02/47763 A1 | 6/2002 |

OTHER PUBLICATIONS

Supplementary Search Report for co-pending European Application No. 03810330.5, mailed Jun. 25, 2010, 3 pages.
PCT International Search Report dated Oct. 14, 2003.
U.S. Appl. No. 60/402,509, filed Aug. 12, 2002.
U.S. Appl. No. 60/377,254, filed May 3, 2002.
U.S. Appl. No. 60/397,195, filed Jul. 22, 2002.
U.S. Appl. No. 10/390,681, filed Mar. 19, 2003.
U.S. Appl. No. 29/166,190, filed Aug. 9, 2002.
First Office Action for co-pending Chinese Application No. 201010185131.3, mailed Nov. 11, 2010, 9 pages.
Office Action fro co-pending European Application No, 03810330.5, mailed Oct. 21, 2010, 6 pages.

* cited by examiner

HEADGEAR ASSEMBLY FOR A RESPIRATORY MASK ASSEMBLY

CROSS-REFERENCE TO PRIORITY APPLICATIONS

This is a continuation of U.S. application Ser. No. 10/655,602, filed Sep. 5, 2003, now U.S. Pat. No. 7,509,958, which claims priority to U.S. Provisional Application Ser. No. 60/424,694 filed Nov. 8, 2002, each incorporated herein by reference in its entirety.

FIELD OF THE INVENTION

The present invention relates to a headgear assembly for use in holding a respiratory mask assembly in position on a patient's face, the mask assembly being used for treatment, e.g., of Sleep Disordered Breathing (SDB) with Non-invasive Positive Pressure Ventilation (NPPV).

BACKGROUND OF THE INVENTION

Respiratory mask assemblies such as the Mirage® nasal mask assembly manufactured by RedMed Ltd. and used for treatment of SDB such as Obstructive Sleep Apnea (OSA) are typically held in position on a patient's head by a headgear assembly. A headgear assembly typically includes a pair of side portions and a rear portion. The side portions are adapted to engage with the patient's mask and the rear portion is adapted to engage the back of the patient's head.

Headgear assemblies are structured to position and stabilize a patient interface, such as a nasal mask, on a patient's face so that a good seal can be maintained. In addition, the headgear assembly should be comfortable so that a patient can wear the mask assembly at night while they sleep. Many prior art headgear assemblies are uncomfortable to wear for long periods. It is desirable that one form of headgear assembly is suitable for a broad range of patients in order to reduce inventory, and ultimately reduce costs.

Completely rigid headgear assemblies are known, but they typically suffer from being uncomfortable to wear for long periods. In addition, because of their rigidity, they typically do not fit a broad range of patients, being suitable only for a subset.

For reasons of costs, it is desirable to be able to cut headgear assemblies from a flat piece of fabric or composite, yet in use the headgear assembly should conform to a complex three-dimensional shape. Hence a problem to overcome is to have a design of headgear assembly which can be easily manufactured by cutting or stamping, and yet in use be able to fit a wide range of head shapes and sizes.

Known forms of headgear assemblies include the Res-Cap™, ResCap™ II and MIRAGE® headgear, as shown in FIGS. 11-16. These headgear assemblies are constructed from fabric or composite layers of fabric and neoprene. Because of the soft flexible nature of the straps in the headgear assembly, there is the possibility of some movement of the headgear assembly on the patient's head, particularly during the course of a night's sleep. Hence, while the headgear assembly may be initially correctly positioned on a patient's head, they may subsequently move to an incorrect position.

A form of connector to enable the headgear assembly to engage with the patient's mask is taught in U.S. Pat. No. 6,374,826 (Gunaratnam et al.), the contents of which are hereby incorporated by reference.

U.S. Pat. No. 6,422,238 (Lithgow) shows a form of headgear assembly including a quick-release mechanism. The contents of the Lithgow patent are hereby incorporated by reference. The headgear assembly taught by Lithgow includes an upper and lower strap in each side portion extending between the patient's face and the rear of the patient's head. The upper straps lie above the ears on the patient's head. The lower straps lie below the ears on the patient's head.

A problem which can occur with prior art mask assemblies, such as the mask assemblies shown in FIGS. 11-16 and taught by Gunaratnam and Lithgow, is that the lower straps of the mask assemblies can ride up the patient's head while in use and cause chafing and irritation of the lower portion of the patient's ears.

SUMMARY OF THE INVENTION

One aspect of the present invention is directed towards a mask assembly having a headgear assembly that offers more comfort to the patient yet does not sacrifice functionality.

Another aspect of the present invention provides a respiratory mask assembly for delivering breathable gas to a patient. The respiratory mask assembly according to one embodiment includes a frame and a headgear assembly removably attachable to the frame. The headgear assembly includes a pair of side portions and a rear portion that interconnects the pair of side portions. The pair of side portions includes at least one strap. The rear portion has at least one strap constructed of at least two layers of material. One of the layers of material has a more rigid construction than the other of the layers of material to resist compression of the at least one strap of the rear portion in a first direction and thereby resist movement of the at least one strap of the pair of side straps in the first direction.

Another aspect of the invention is to provide a means for maintaining flexible headgear straps of a mask assembly in correct relative position on a patient's head in use.

Another aspect of the invention is to provide a comfortable headgear assembly for a mask assembly which fits a wide range of head shapes and sizes.

Another aspect of the invention is to provide a comfortable headgear assembly of a mask assembly which fits a wide range of patients and can be cut from a flat piece of fabric.

Other aspects, features and advantages of this invention will become apparent from the following detailed description when taken in conjunction with the accompanying drawings, which are part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

Figure 1:
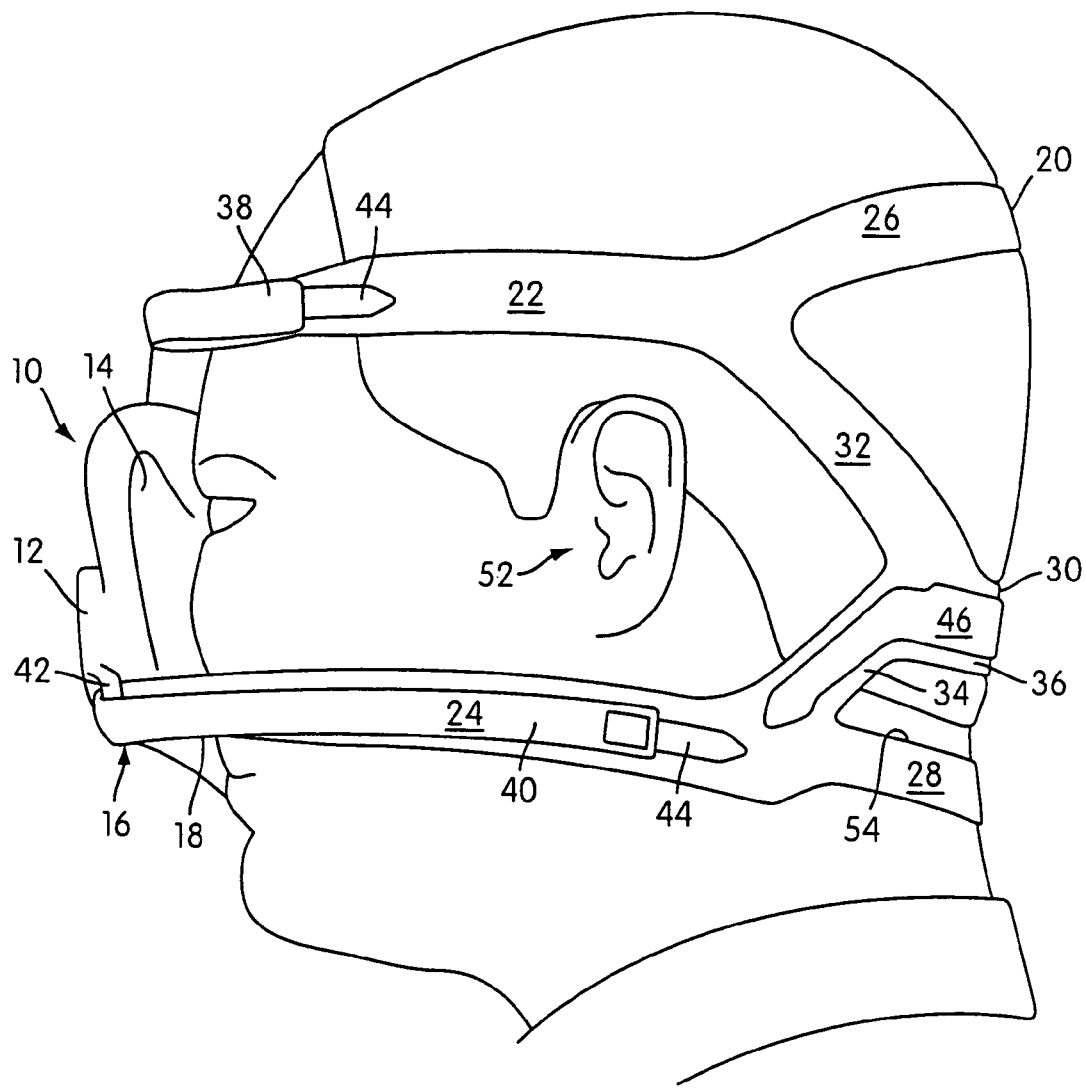
FIG. 1 is a side view illustrating a mask assembly having a headgear assembly constructed in accordance with an embodiment of the invention mounted on a patient's head.

FIG. 1 shows a respiratory mask assembly 10 that includes a frame 12 and a cushion 14 that may be permanently or removably connected to the frame 12. A headgear assembly 16 is removably attached to the frame 12 and is structured to maintain the frame 12 and cushion 14 in a desired adjusted position on a patient's face. In the illustrated embodiment, the mask assembly 10 is a nasal mask structured to deliver breathable gas to a patient's nose. However, the mask assembly 10 may be a nasal and mouth mask or the mask assembly 10 may be a full-face mask.

As shown in FIGS. 1-4, the headgear assembly 16 includes two side portions 18 with a rear portion 20 connecting the side portions 18. Each side portion 18 comprises an upper side strap 22 and a lower side strap 24. The rear portion 20, which interconnects the two side portions 18, includes a curved upper strap 26, a lower strap 28, and an intermediate strap arrangement 30 therebetween. The intermediate strap arrangement 30 is generally H-shaped and has a pair of upper straps 32, a pair of lower straps 34, and a cross-bar strap 36. The upper straps 32 are angled with respect to the curved upper strap 26 and the lower straps 34 are angled with respect to the lower strap 28. However, the straps of the headgear assembly 16 may have any suitable configuration to maintain the frame 12 and cushion 14 in a desired adjusted position on a patient's face. For example, the upper strap 26 may not be curved with respect to the upper straps 22 and the intermediate strap arrangement 30 may have any suitable shape, i.e., not H-shaped.

Figure 4:
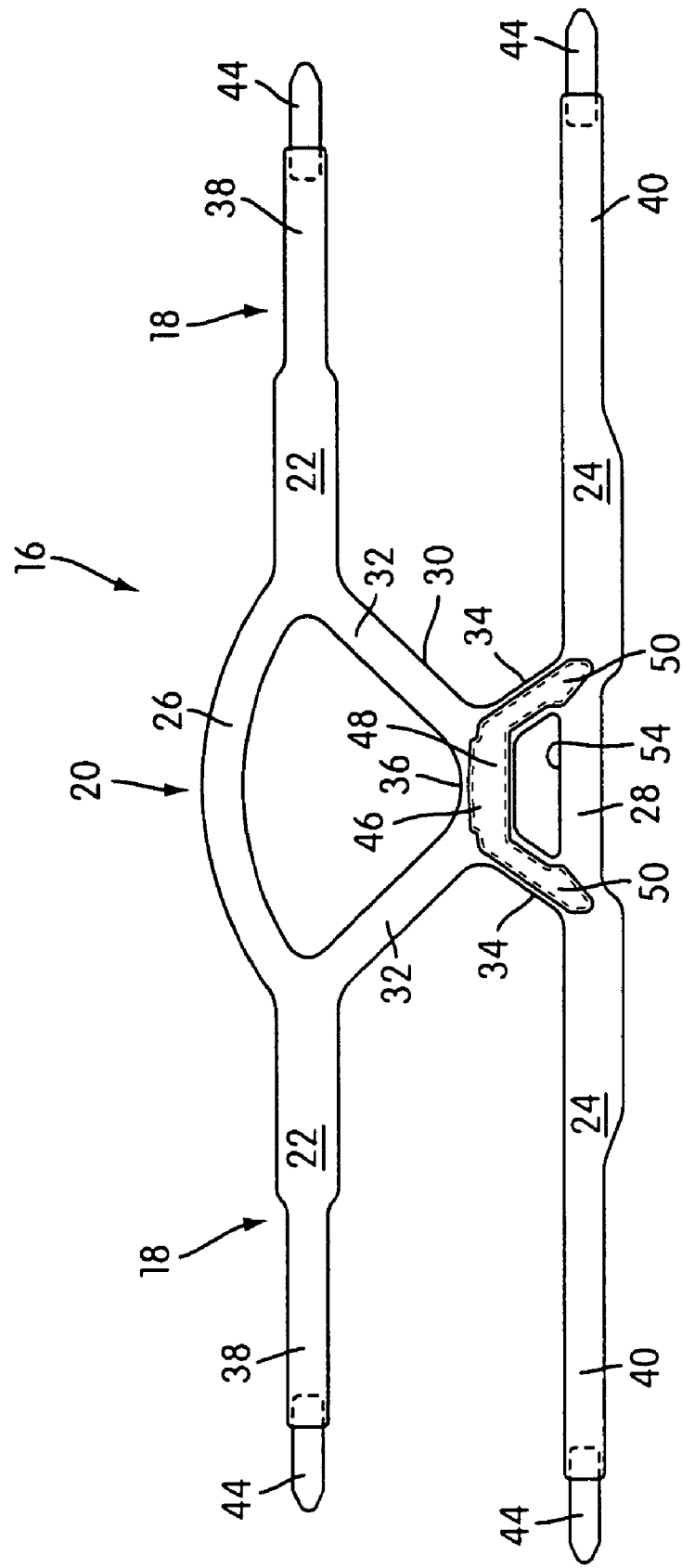
FIG. 4 is a top view illustrating the headgear assembly of FIG. 1 laid flat.

Each upper side strap 22 is removably connected to an upper portion of the frame 12 and each lower side strap 24 is removably connected to a lower portion of the frame 12. As shown in FIG. 4, the end portion 38, 40 of each upper and lower strap 22, 24, respectively, has a reduced width that enables each upper and lower strap 22, 24 to be wrapped around a respective clip structure 42 (see FIG. 1) provided on the frame 12. Fastening of the upper and lower straps 22, 24 to the frame 12 may be assisted by use of a hook and loop material, such as VELCRO®. As shown in FIG. 4, the free end of each upper and lower strap 22, 24 includes a strip of hook material 44 attached thereto by stitching, for example. The upper and lower straps 22, 24 are constructed of a loop material that engages the strip of hook material 44 when the upper and lower straps 22, 24 are connected to the frame 12.

However, the upper and lower straps 22, 24 may be connected to the frame 12 in any other suitable manner. For example, the upper and lower straps 22, 24 may include locking clips attached thereto that are adapted to interlockingly engage with the frame 12. Alternatively, the upper and lower straps 22, 24 may be magnetically coupled with the frame 12 so as to interconnect the frame 12 and headgear assembly 16. Further, the frame 12 may include a forehead support movably mounted to an upper portion thereof. In such an arrangement, the upper straps 22 may be removably connected to clip structures provided on the forehead support.

Figure 7:
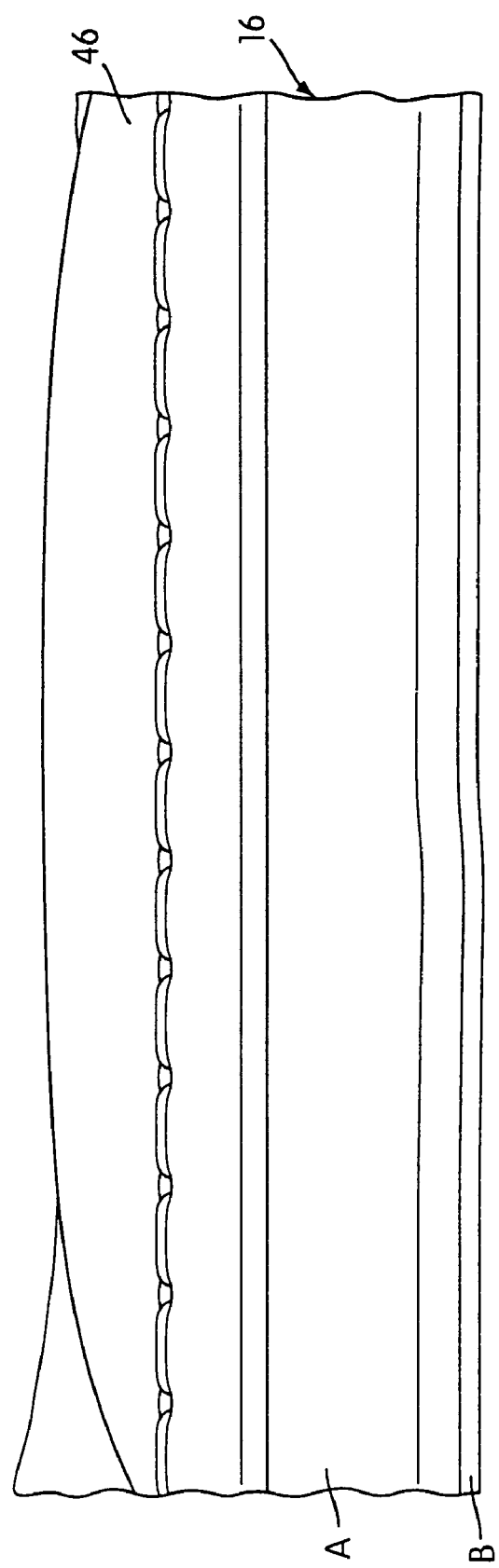
FIG. 7 is an enlarged photographic side view illustrating an embodiment of a stiffener of the headgear assembly of FIG. 1.

The straps of the headgear assembly 16 are constructed from a soft, flexible composite material such as Breathe-O-Prene™ manufactured by Accumed Technologies, Inc. As shown in FIG. 7, the straps include two layers of material A, B with one of the layers A having a loop material to facilitate the connection with the strip of hook material 44 provided on the free ends the upper and lower straps 22, 24. However, the straps may be constructed from any other suitable soft, flexible material.

In the illustrated embodiment, a stiffener 46 is attached to the rear portion 20 of the headgear assembly 16. As shown in FIGS. 2 and 4-6, the stiffener 46 has a general C-shape including a body 48 and a pair of arm members 50. The stiffener 46 is attached to the H-shaped intermediate strap arrangement 30 such that the body 48 of the stiffener 46 extends along the cross-bar strap 36 and the arm members 50 of the stiffener 46 extend along respective lower straps 34. The body 48 has a width that is greater than a width of the arm members 50. Further, the free ends of the arm members 50 have a greater width than the remaining portion of the arm members 50. However, the stiffener 46 may have any suitable structure and width dimensions. The stiffener 46 is constructed from a semi-rigid skin-compatible material such as thermoplastics, e.g., nylon or polyester or a thermoplastic elastomer, e.g. santoprene. The stiffener 46 has a thickness in the range of 0.8 mm to 1.5 mm, preferably 1 mm.

Figure 5:
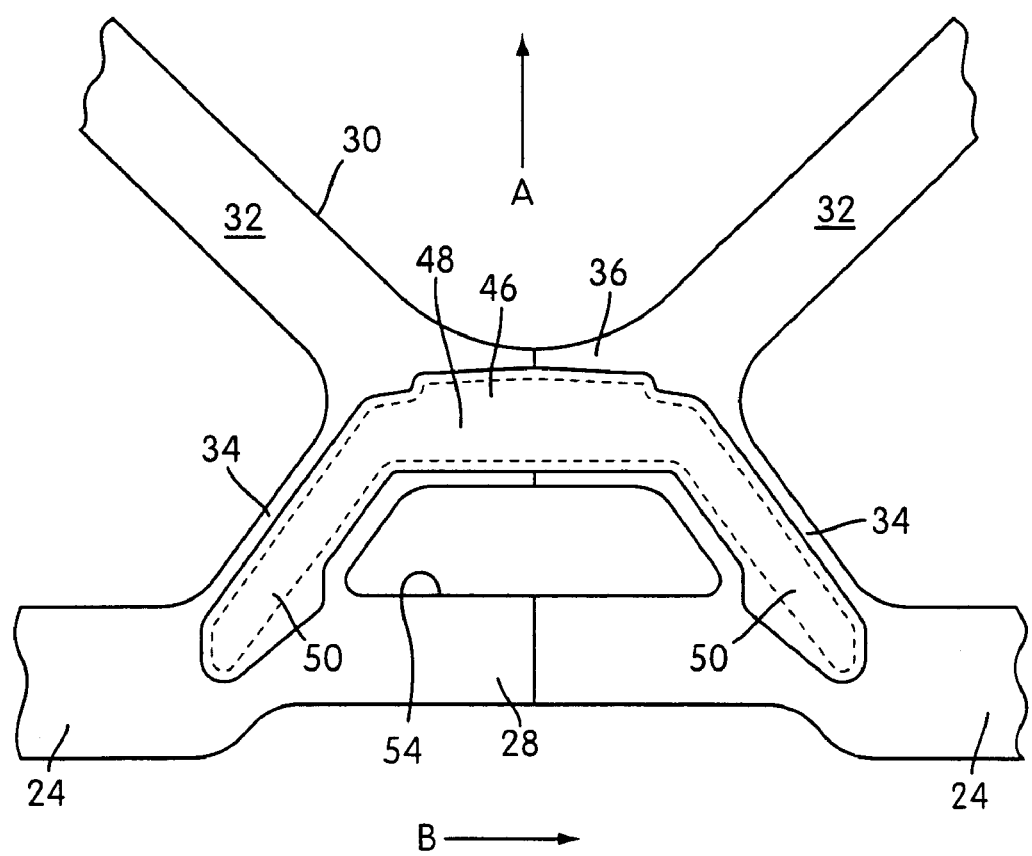
FIG. 5 is an enlarged top view illustrating an embodiment of a stiffener of the headgear assembly of FIG. 1.
Figure 6:
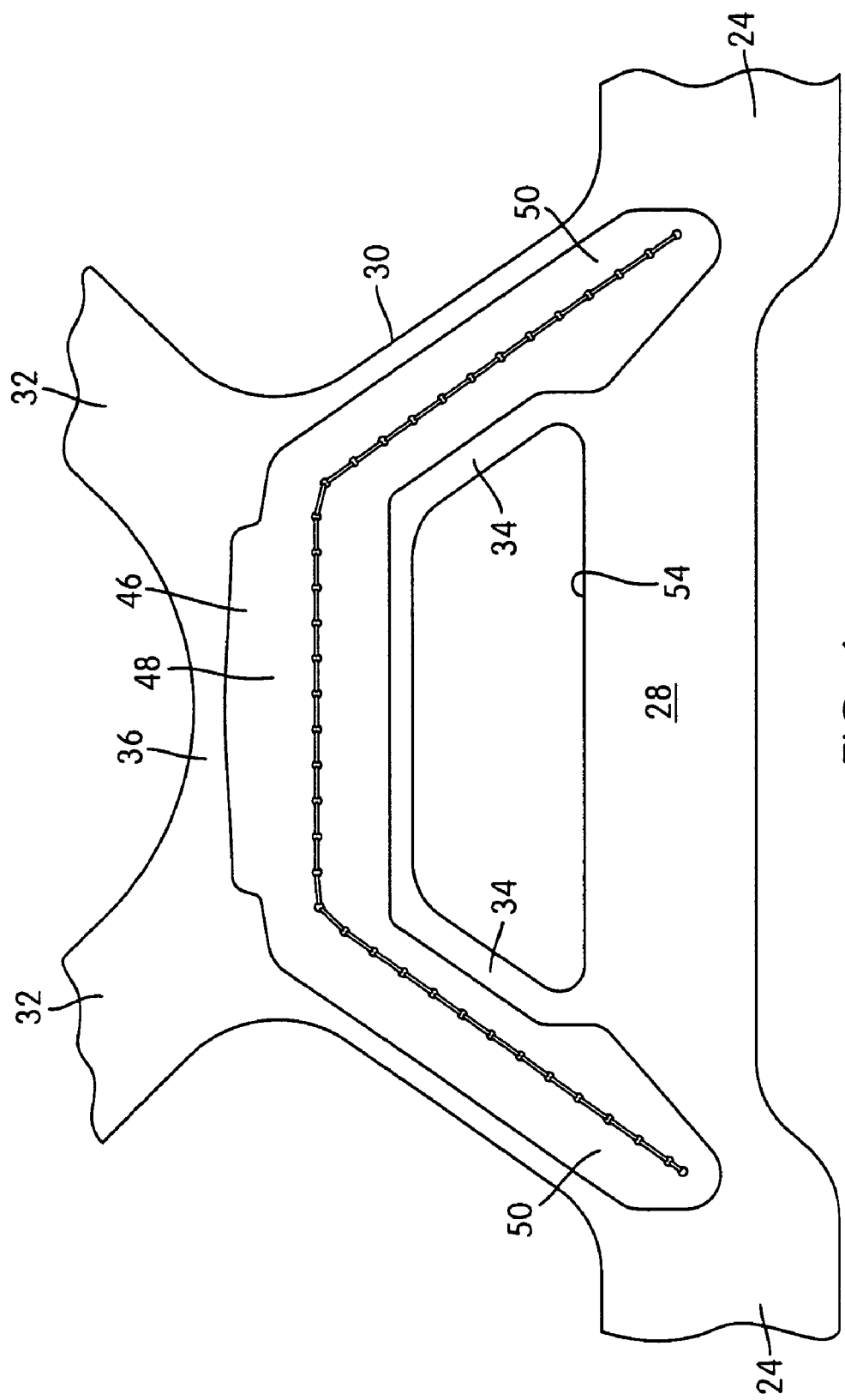
FIG. 6 is an enlarged photographic top view illustrating an embodiment of a stiffener of the headgear assembly of FIG. 1.

The stiffener 46 is attached to the corresponding straps 34, 36 with adhesives, stitching, or other known attachment mechanisms or by semi-permanent means such as velcro, pocket sleeve, etc. As shown in FIG. 5, the stiffener 46 is secured to the straps 34, 36 by stitching around the periphery of the stiffener 46. As shown in FIG. 6, the stiffener 46 is secured to the straps by stitching an intermediate portion of the stiffener 46. FIG. 7 is an enlarged view that illustrates the stiffener 46 secured to the straps by stitching. The stitch line is in the range of 2-3 mm, preferably 2.5 mm, from the edge of the stiffener 46.

The stiffener 46 is narrower than the straps 34, 36 so that when the stiffener 46 is attached to the straps 34, 36, the softer material of the straps 34, 36 extends beyond the more rigid material of the stiffener 46, thereby preventing or at least reducing the opportunity for contact between the patient and the more rigid material of the stiffener 46 that could cause irritation or discomfort.

The stiffener 46 adds to the rigidity of the headgear assembly 16 in certain planes and directions, which assists in stabilizing the mask assembly 10 on the head of the patient during use. In other planes and directions, the headgear assembly 16 has a different rigidity.

Figure 2:
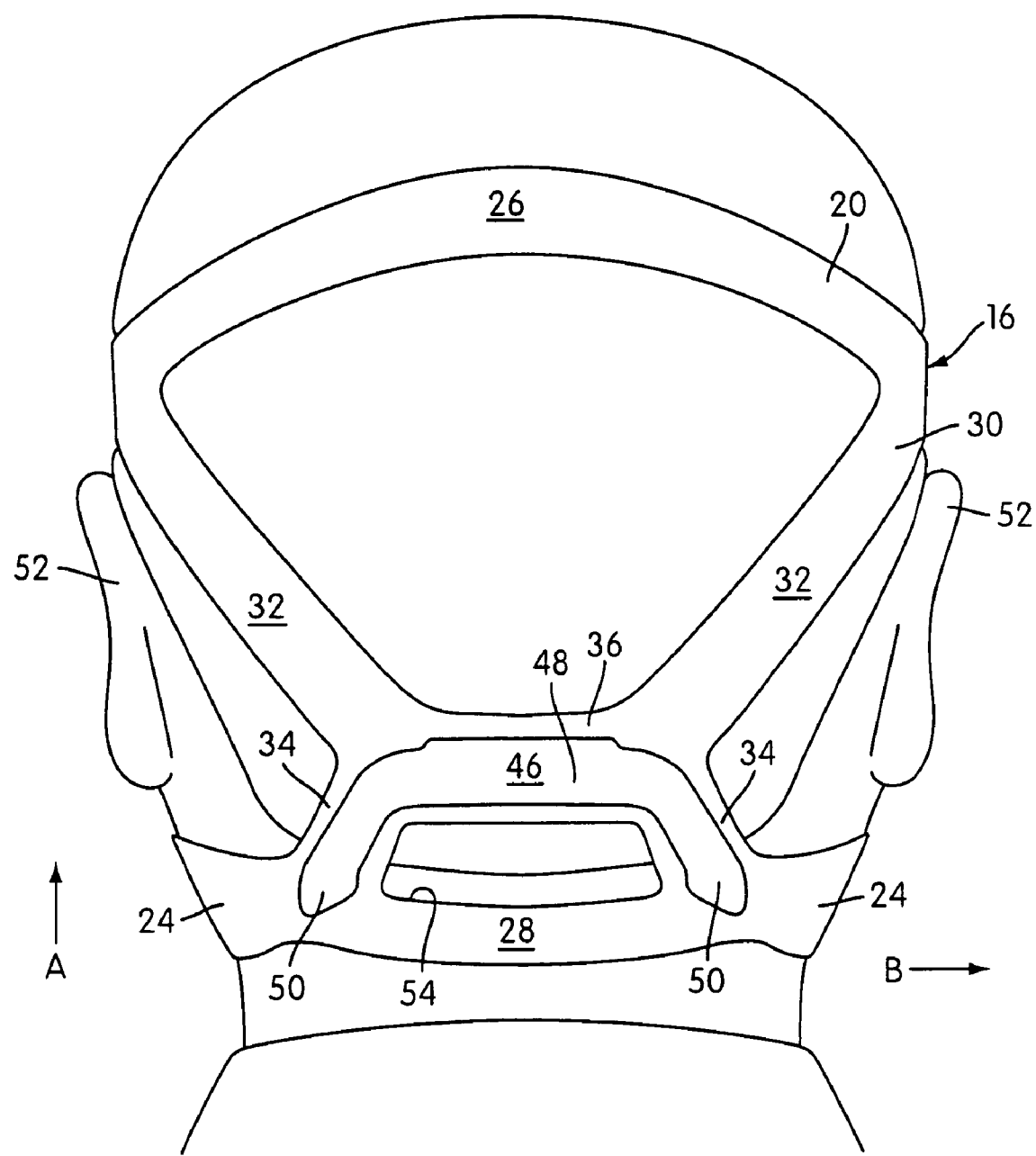
FIG. 2 is a rear view illustrating the headgear assembly of FIG. 1 mounted on a patient's head.
Figure 3:
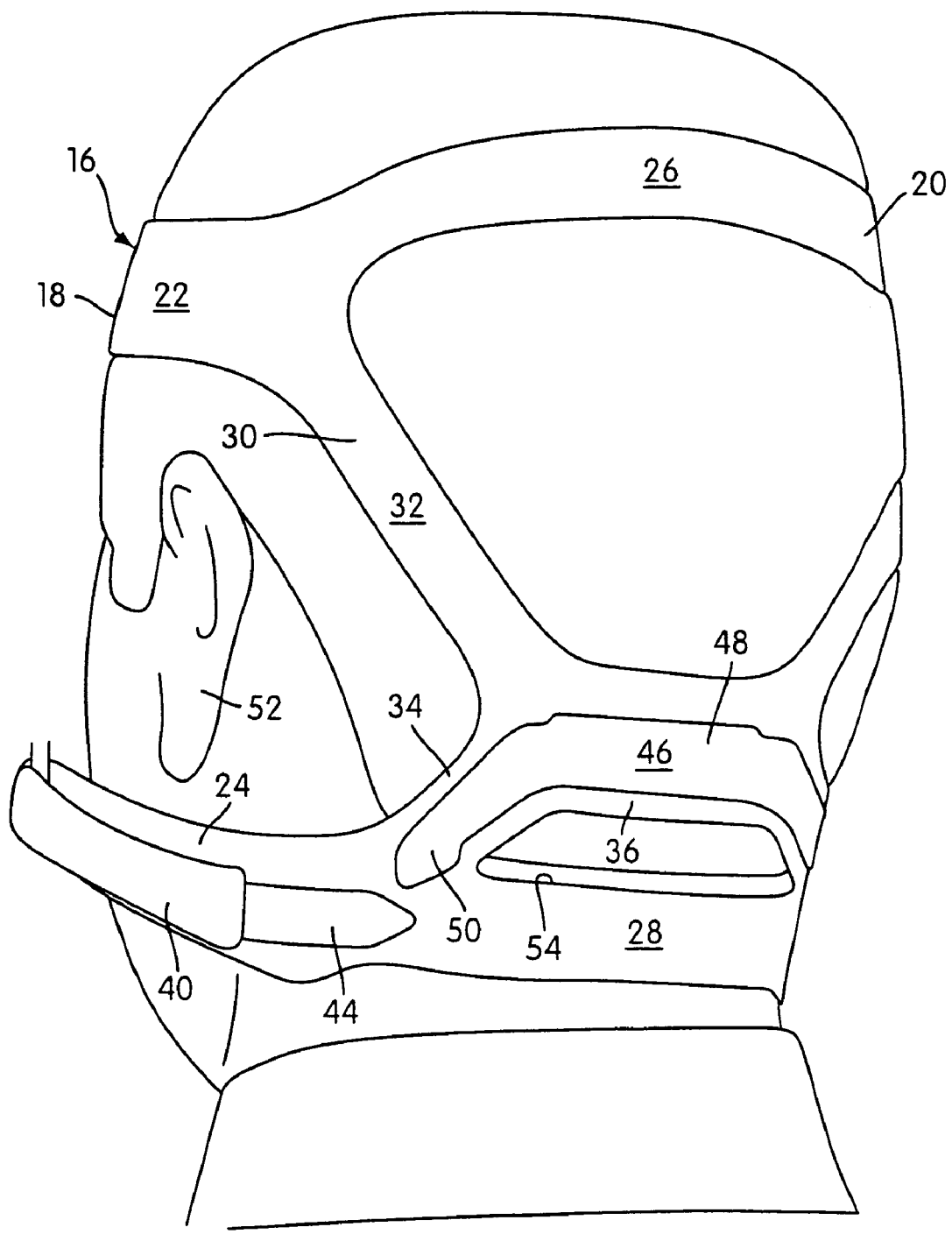
FIG. 3 is a rear perspective view illustrating the headgear assembly of FIG. 1 mounted on a patient's head.

For example, the stiffener 46 reduces the flexibility of the straps 34, 36 at the back of the patient's head along the direction of arrow A or in a reverse direction of arrow A, as shown in FIG. 2. The presence of the stiffener 46 stops compression of the straps 34, 36 along the reverse direction of arrow A. In this way, the straps 34, 36 and stiffener 46 should be able to resist the riding up of the lower straps 24 towards the patient's ears 52. In general, the straps 34, 36 and stiffener 46 should be able maintain their positions with respect to the head of the patient when the straps 34, 36 and stiffener 46 are connected to the frame 12. Thus, the likelihood that the lower straps 24 will ride up into the lower portion of the ears 52 of the patient is reduced.

Further, the headgear assembly 16 is shaped to avoid interference with the patient's ears 52. In particular, the upper side strap 22 is connected to the frame 12 above the patient's eyes and patient's ears 52. The lower side strap 24 is connected to the frame 12 and extends below the patient's ear 52. The upper straps 32 and lower straps 34 interconnect the upper and lower straps 22, 24 and are angled sufficiently away from the patient's ears 52. Also, the upper and lower straps 32, 34 are of sufficient length to space the upper and lower straps 22, 24 from the patient's ears 52. Due to the added rigidity provided by the stiffener 46, all the straps of the headgear assembly 16 are better able to maintain a predetermined shape. The thickness of the stiffener 46 may vary across its profile to modify flexibility characteristics, for example, thicker regions may be stiffer.

On the other hand, a certain degree of flexibility of the headgear assembly 16 is provided such that variations in patient physiology can be accommodated to a certain degree. For example, the lower strap 28 has relatively more flexibility along arrow direction B or its reverse direction than straps 34, 36 with the stiffener 46 attached.

The H-shaped intermediate strap arrangement 30 of the headgear assembly 16 also helps maintain the headgear assembly 16 in a desired adjusted position on the patient. As shown in FIG. 1, the curved upper strap 26 extends across a rear upper portion of the patient's head and the lower strap 28 and cross-bar strap 36 extend across a rear lower portion of the patient's neck and head, respectively. More specifically, the curved upper strap 26 is structured to engage a posterior portion of the parietal bone of the patient's head in order to prevent downward movement of the headgear assembly 16 opposite the direction of arrow A in FIG. 2. The cross-bar strap 36 is structured to engage a lower portion of the occipital bone of the patient's head and the lower strap 28 is structured to engage a rear upper portion of the patient's neck. As a result, the cross-bar strap 36 and the lower strap 28 prevent upward movement of the headgear assembly 16 in the direction of arrow A in FIG. 2. Moreover, the stiffener 46 is structured to resist the riding up of the lower straps 34 and hence the lower straps 24 towards the patient's ears 52. However, the intermediate strap arrangement 30 may have any suitable configuration to maintain the frame 12 and cushion 14 in a desired adjusted position on a patient's face.

Further, the straps 28, 34, and 36 form an opening 54 therebetween that can accommodate any skin folds of a patient which may extend through the opening 54. Specifically, movement of the patient's head can create a fold of skin adjacent the patient's neck. The straps 28, 34, and 36 are structured and positioned on the patient's head such that any skin folds will extend through the opening 54 and not adversely affect the positioning of the headgear assembly 16 on the patient's head. The opening 54 formed between the straps 28, 34, and 36 may have any suitable shape, i.e., trapezoidal or non-trapezoidal shape. The reduced width of strap 28 allows it to stretch over the fatter lower neck, that is, there is a different stretch between strap 36 and strap 28.

Figure 8:
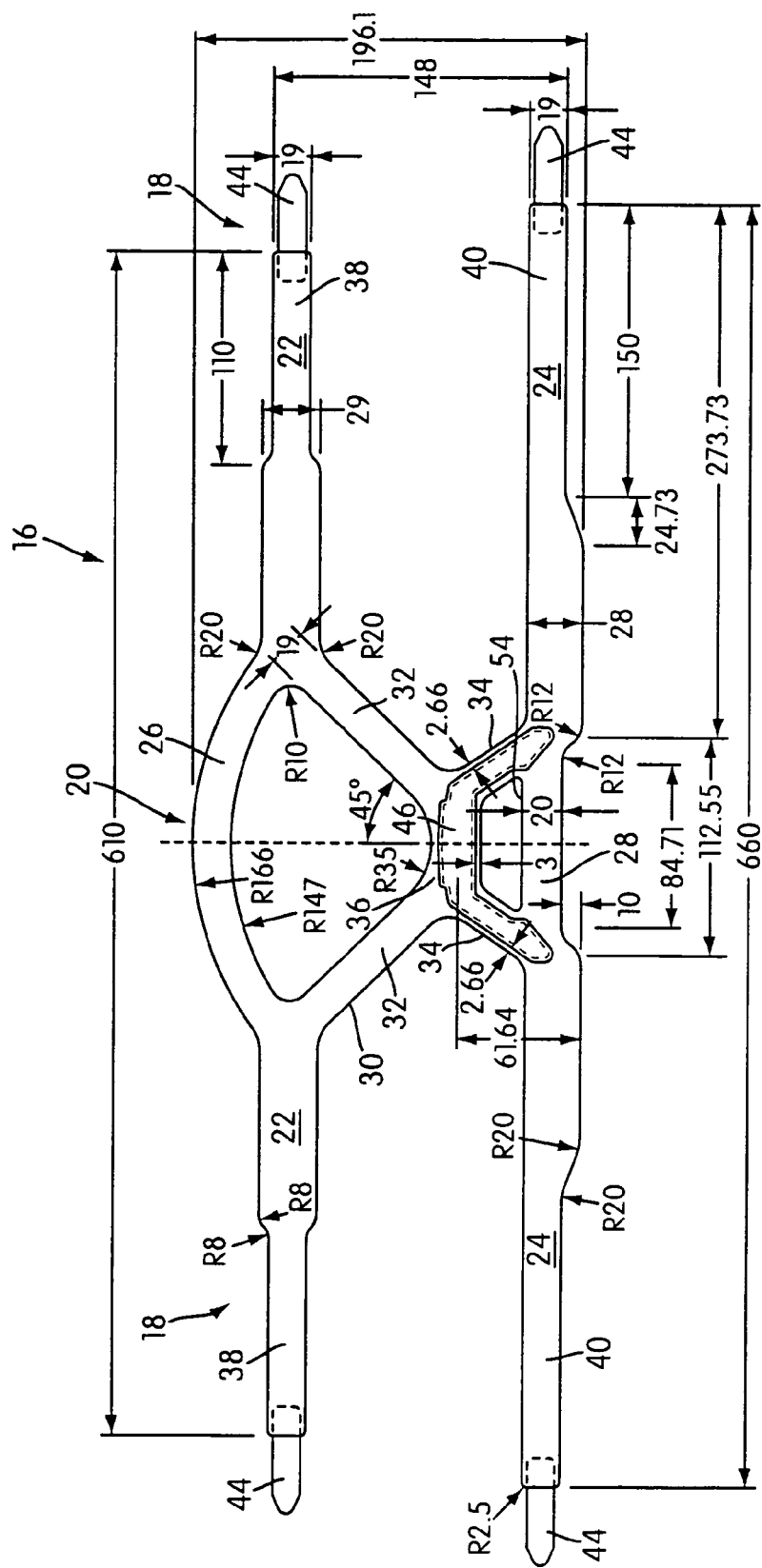
FIG. 8 is a top view illustrating the headgear assembly of FIG. 1 laid flat and showing typical dimensions of an embodiment (R-radius)

FIG. 8 illustrates dimensions of an embodiment of the headgear assembly 16. For example, the overall length of the headgear assembly 16 is in the range of 640-680 mm, preferably 660 mm and the overall height of the headgear assembly 16 is in the range of 175-215 mm, preferably 196.1 mm. The upper straps 32 are angled in the range of 40-50°, preferably 45°, with respect to the upper straps 22 and have a width in the range of 16-22 mm, preferably 19 mm. The curved upper strap 26 has a radius of curvature in the range of 145-170 mm, preferably 166 mm. Further, the lower strap 28 has a width in the range of 17-23 mm, preferably 20 mm, and the end portions 38, 40 of the upper and lower straps 22, 24 have a width in the range of 16-23 mm, preferably 19 mm. In an embodiment of the headgear assembly 16, the dimensions illustrated in FIG. 8 vary ±10%.

Figure 9:
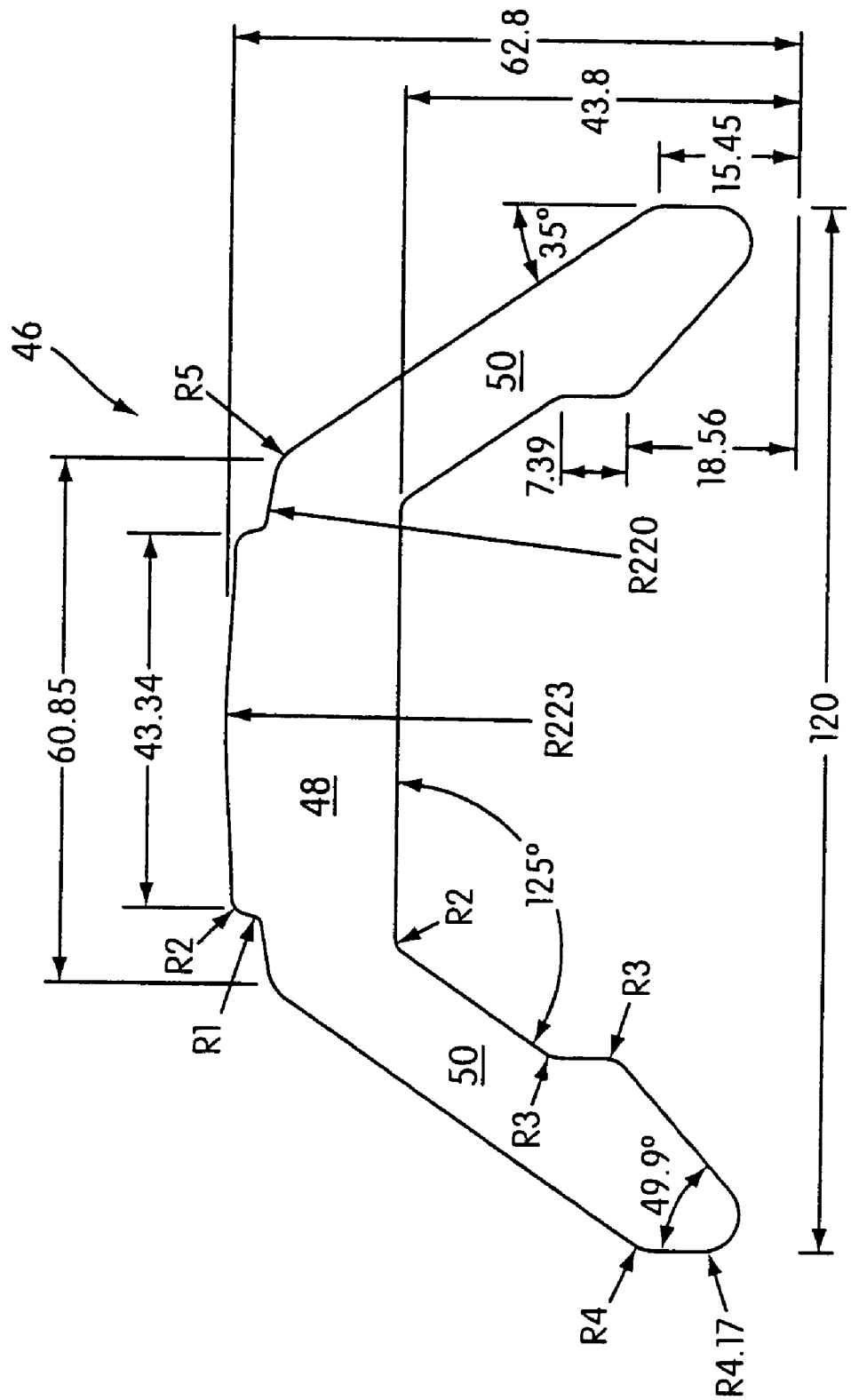
FIG. 9 is a top view illustrating an embodiment of a stiffener of the headgear assembly of FIG. 1 and showing typical dimensions of an embodiment (R-radius)

FIG. 9 illustrates dimensions of an embodiment of the stiffener 46. For example, the overall length of the stiffener 46 is in the range of 100-140 mm, preferably 120 mm and the overall height of the stiffener 46 is in the range of 40-80 mm, preferably 62.8 mm. The arm members 50 are angled in the range of 110-140°, preferably 125°, with respect to the body 48. In an embodiment of the stiffener 46, the dimensions illustrated in FIG. 9 vary ±10%.

Figure 10:
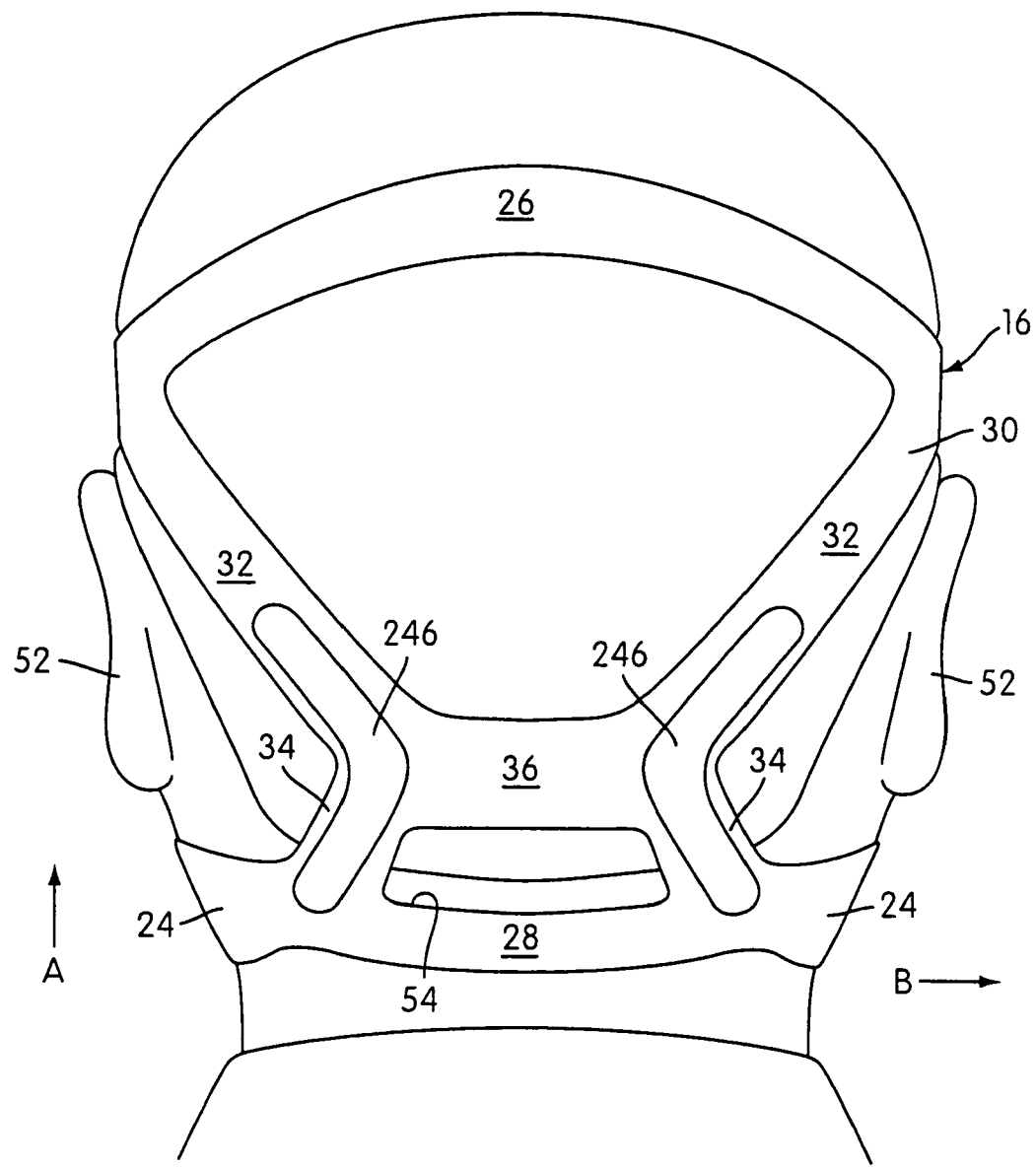
FIG. 10 is a rear view illustrating a headgear assembly constructed in accordance with another embodiment of the invention mounted on a patient's head.
Figure 11:
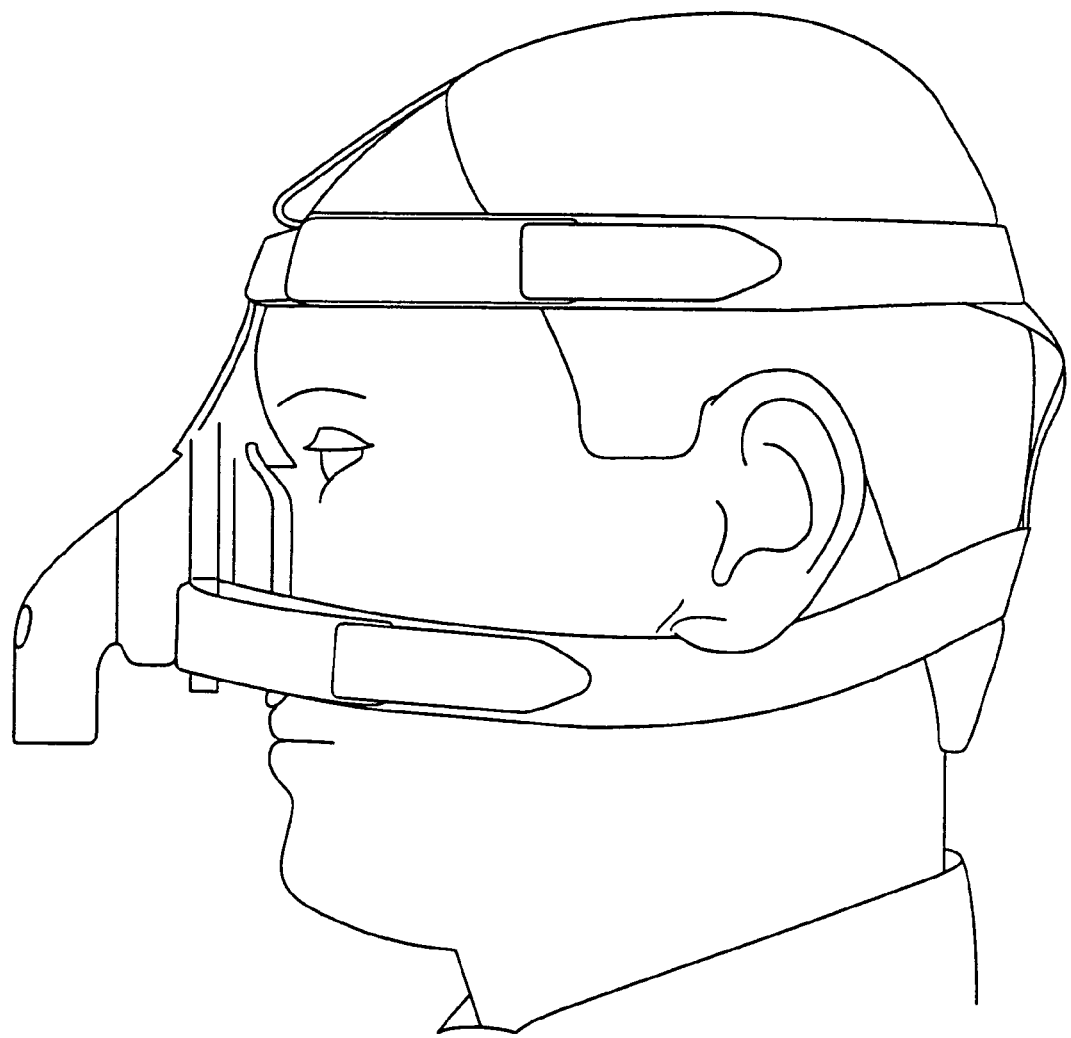
FIG. 11 is a side view of a prior art ResCap™ headgear assembly.
Figure 12:
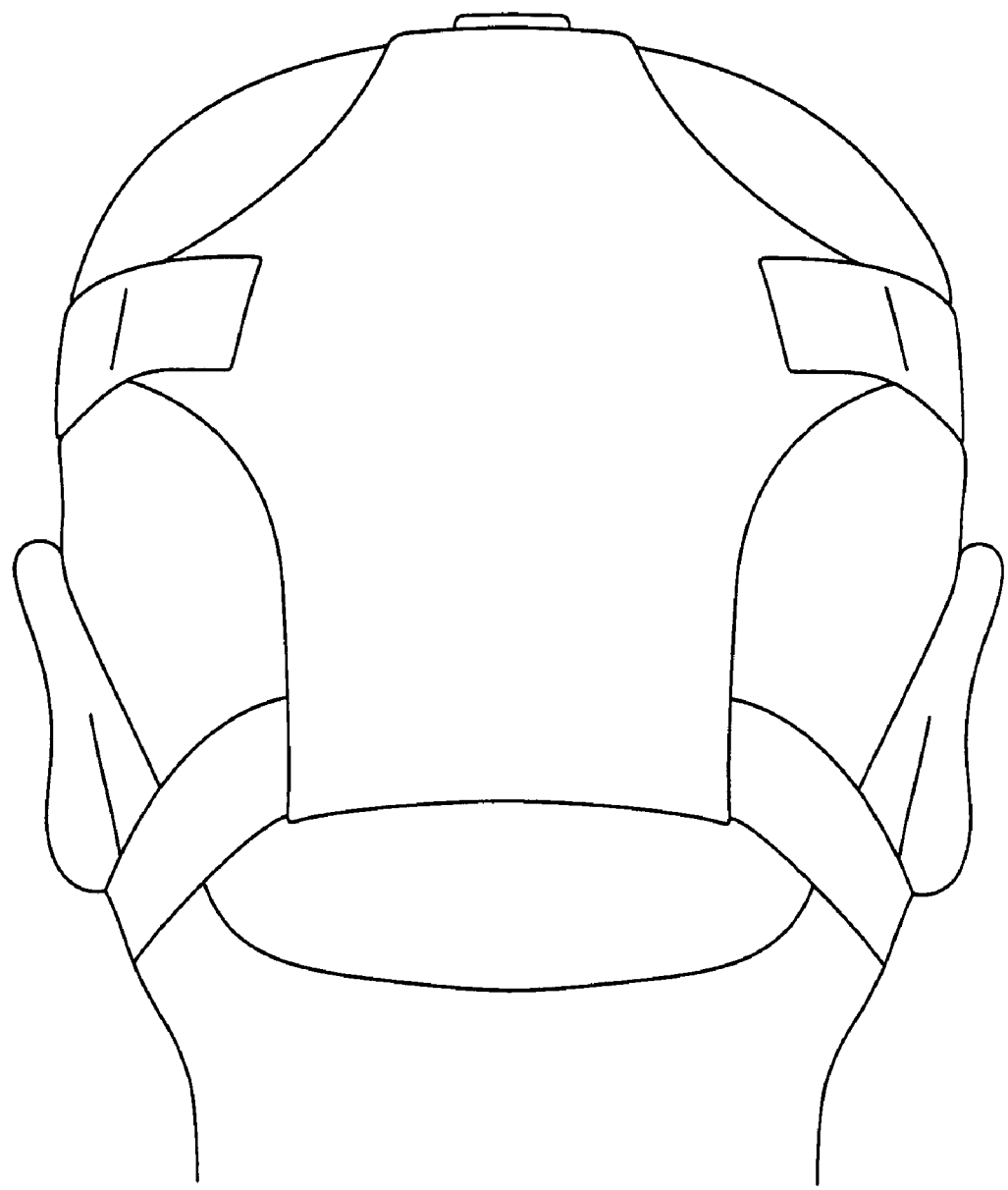
FIG. 12 is a rear view of a prior art ResCap™ headgear assembly.
Figure 13:
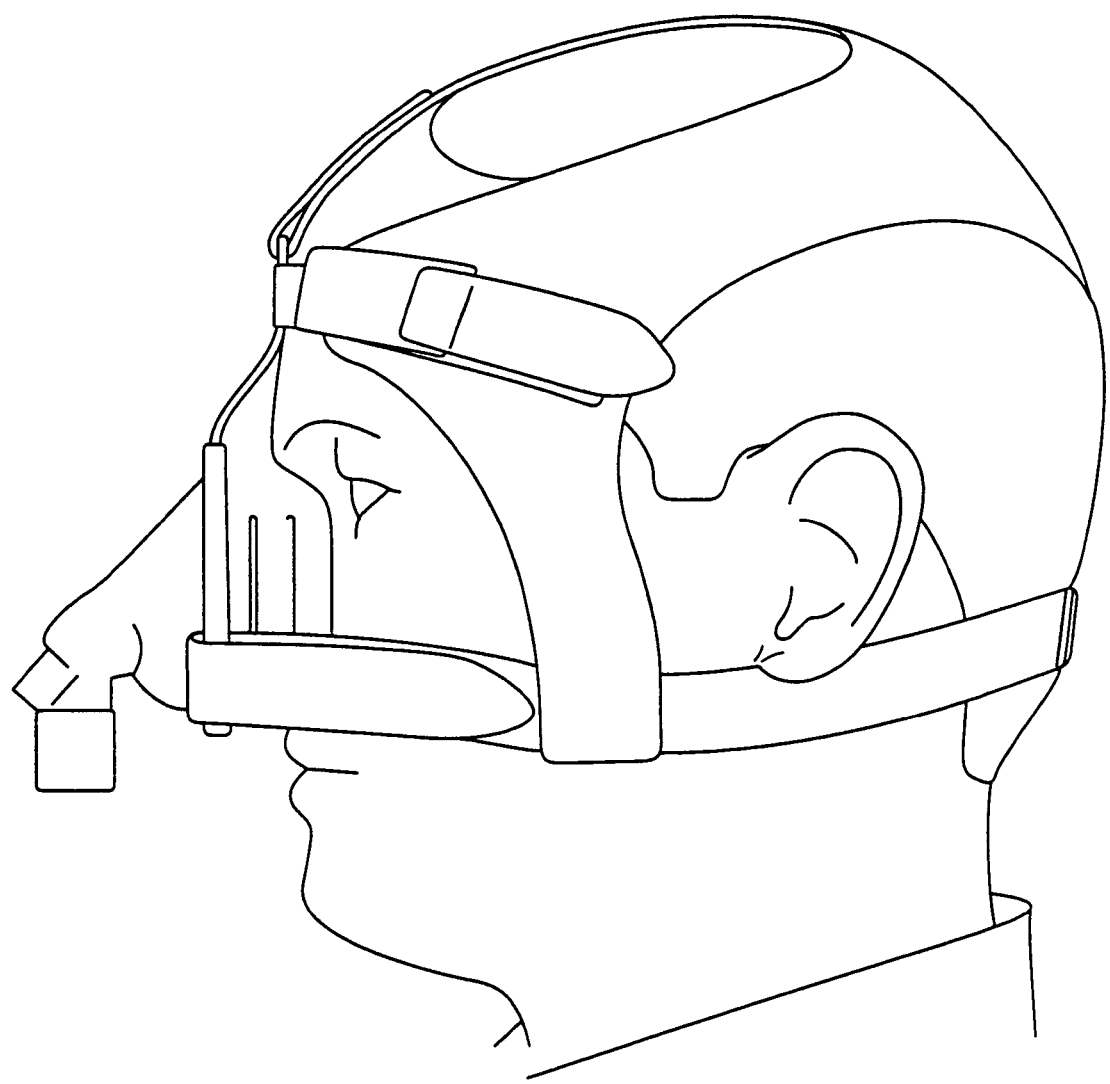
FIG. 13 is a side view of a prior art ResCap™ II headgear assembly.
Figure 14:
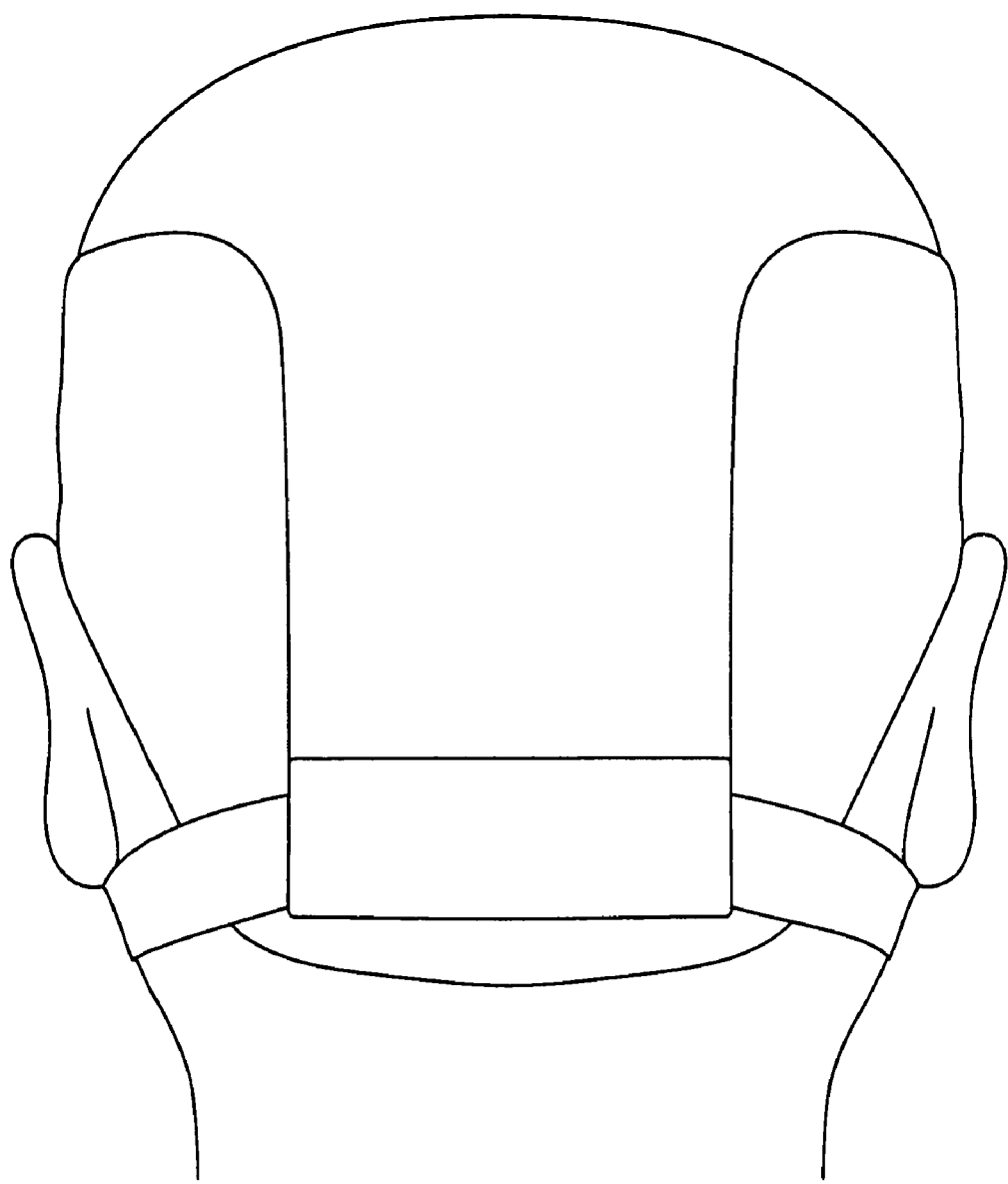
FIG. 14 is a rear view of a prior art ResCap™ II headgear assembly.
Figure 15:
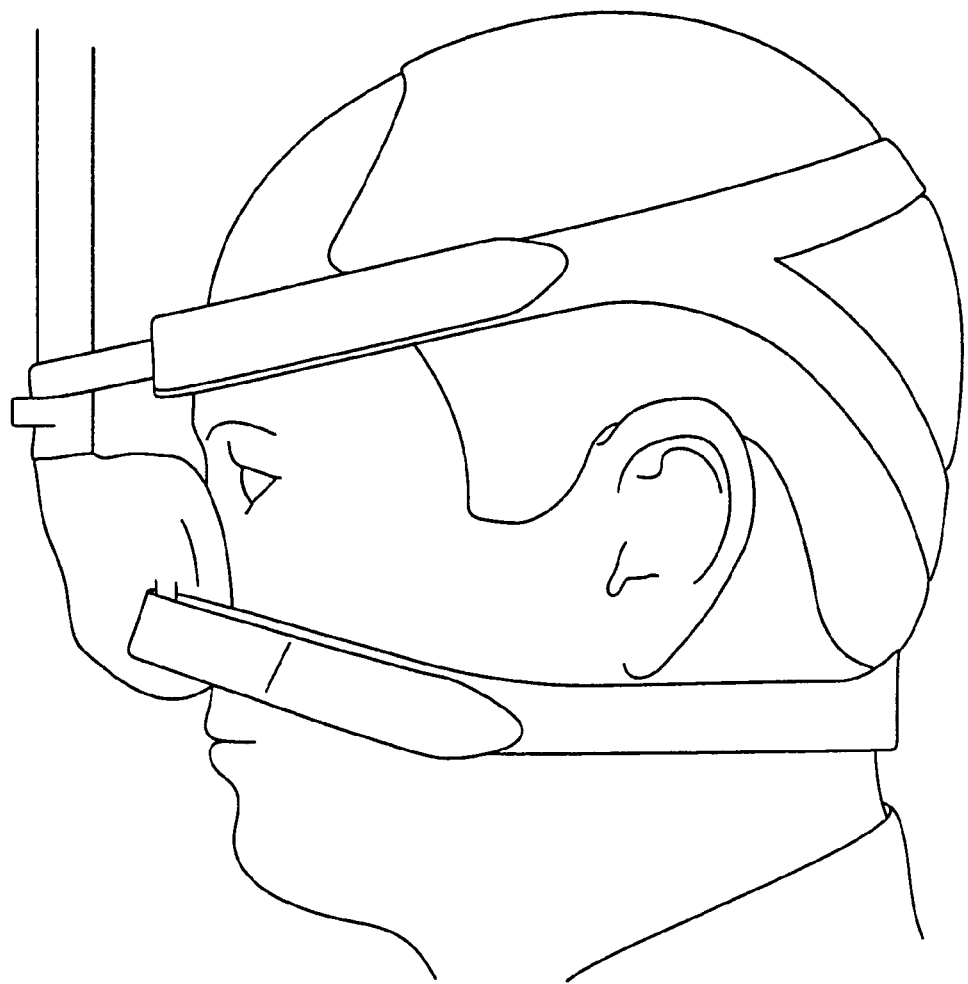
FIG. 15 is a side view of a prior art MIRAGE® headgear assembly.
Figure 16:
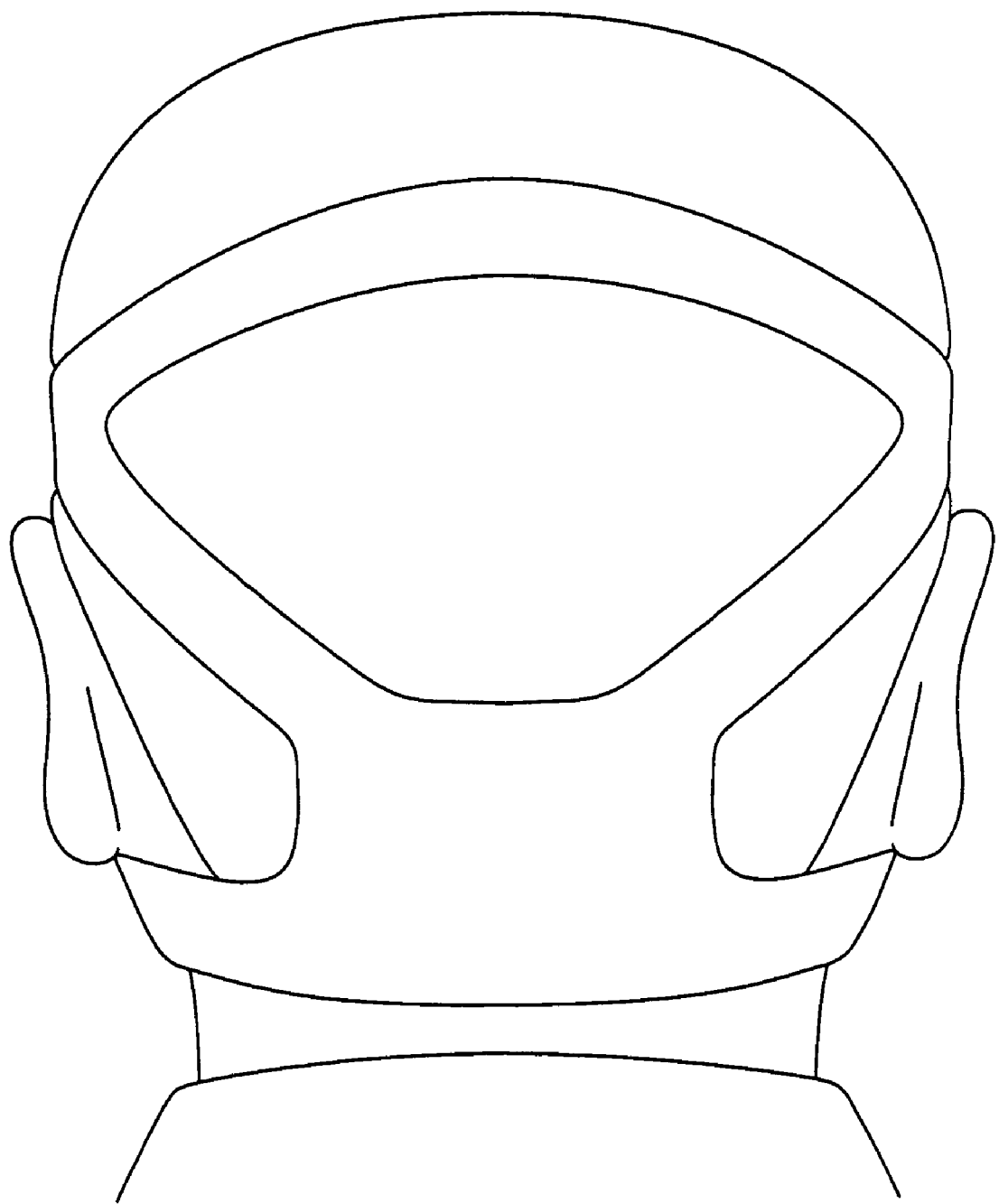
FIG. 16 is a rear view of a prior art MIRAGE® headgear assembly.

FIG. 10 illustrates another embodiment of the stiffener, indicated as 246. In this embodiment, the stiffener is in the form of a pair of arcuate-shaped stiffeners 246. Each stiffener 246 extends along the upper strap 32, across the cross-bar strap 36, and along the lower strap 34. Similar to the stiffener 46, the stiffeners 246 reduces the flexibility of the straps 32, 34, and 36 at the back of the patient's head along the direction of arrow A or in a reverse direction of arrow A, so as to resist the riding up of the lower straps 24 towards the patient's ears 52.

The straps of the headgear assembly 16 and the stiffener 46, 246 may be formed of a single material, so long as patient comfort and the appropriate rigidity/flexibility are maintained.

It can thus be appreciated that the aspects of the present invention have been fully and effectively accomplished. The foregoing specific embodiments have been provided to illustrate the structural and functional principles of the present invention, and are not intended to be limiting. To the contrary, the present invention is intended to encompass all modification, alterations and substitutions within the spirit and scope of the detailed description.

What is claimed is:

1. A headgear assembly for stabilizing and positioning a respiratory mask assembly on a patient's head, comprising:
   a pair of side straps;
   at least two rear straps including at least an upper rear strap and a lower rear strap, wherein at least one of the at least two rear straps has a curved portion of a predetermined radius, wherein the predetermined radius is measured when the headgear assembly is laid out flat; and
   an intermediate strap arrangement positioned between the at least two rear straps, wherein the intermediate strap arrangement includes a pair of upper straps angled relative to the upper rear strap and a pair of lower straps angled relative to the lower rear strap.

2. A headgear assembly for stabilizing and positioning a respiratory mask assembly on a patient's head, comprising:
   a pair of side straps;
   at least two rear straps including at least an upper rear strap and a lower rear strap, wherein at least one of the at least two rear straps has a curved portion of a predetermined radius, wherein the predetermined radius is measured when the headgear assembly is laid out flat; and
   an intermediate strap arrangement positioned between the at least two rear straps, wherein the intermediate strap arrangement includes a pair of upper straps angled relative to the upper rear strap and a pair of lower straps angled relative to the lower rear strap, wherein the curved portion extends between and connects to the upper straps of the intermediate strap arrangement.

3. The headgear assembly according to claim 2, wherein the curved portion is structured to engage a posterior portion of the parietal bone of the patient's head in use.

4. The headgear assembly according to claim 2, wherein the at least two rear straps are not parallel to one another.

5. The headgear assembly according to claim 2, wherein the intermediate strap arrangement is generally H-shaped.

6. The headgear assembly according to claim 2, wherein the pair of upper and lower straps converge towards and join with a cross bar strap.

7. The headgear assembly according to claim 2, wherein the predetermined radius is in the range of 145-170 mm.

8. The headgear assembly according to claim 7, wherein the upper rear strap has a radius of curvature of 166 mm.

9. The headgear assembly according to claim 2, wherein the pair of upper straps of the intermediate strap arrangement and the upper rear strap at least partially define a first opening.

10. The headgear assembly according to claim 9, wherein the lower rear strap and the pair of lower straps of the intermediate strap arrangement at least partially define a second opening.

11. The headgear assembly according to claim 2, wherein an overall length of the headgear assembly is in the range of 640-680 mm and an overall height of the headgear assembly is in the range of 175-215 mm.

12. The headgear assembly according to claim 11, wherein an overall length of the headgear assembly is 660 mm and an overall height of the headgear assembly is 196.1 mm.

13. The headgear assembly according to claim 2, wherein the pair of upper straps of the intermediate strap arrangement are angled with respect to the upper rear strap in the range of 40-50° and have a width in the range of 16-22 mm.

14. The headgear assembly according to claim 13, wherein the pair of upper straps of the intermediate strap arrangement are angled with respect to the upper rear strap at an angle of 45° and have a width of 19 mm.

15. The headgear assembly according to claim 2, wherein the intermediate strap arrangement interconnects the upper rear strap and the lower rear strap.

16. The headgear assembly according to claim 2, wherein the at least two rear straps comprise generally flat, flexible composite material.

17. A headgear assembly for stabilizing and positioning a respiratory mask assembly on a patient's head, comprising:
a pair of side straps;
at least two rear straps including at least an upper rear strap and a lower rear strap, wherein at least one of the at least two rear straps has a curved portion of a predetermined radius, wherein the predetermined radius is measured when the headgear assembly is laid out flat; and
an intermediate strap arrangement positioned between and connects or bridges the at least two rear straps, wherein the intermediate strap arrangement includes a pair of upper straps angled relative to the upper rear strap and a pair of lower straps angled relative to the lower rear strap.

18. The headgear assembly according to claim 17, wherein the curved portion is structured to engage a posterior portion of the parietal bone of the patient's head in use.

19. The headgear assembly according to claim 17, wherein the at least two rear straps are not parallel to one another.

20. The headgear assembly according to claim 17, wherein the intermediate strap arrangement is generally H-shaped.

21. The headgear assembly according to claim 17, wherein the pair of upper and lower straps converge towards and join with a cross bar strap.

22. The headgear assembly according to claim 17, wherein the predetermined radius is in the range of 145-170 mm.

23. The headgear assembly according to claim 22, wherein the predetermined radius is 166 mm.

24. The headgear assembly according to claim 17, wherein the upper straps of the intermediate strap arrangement and the upper rear strap at least partially define a first opening.

25. The headgear assembly according to claim 24, wherein the lower rear strap and the pair of lower straps of the intermediate strap arrangement at least partially define a second opening.

26. The headgear assembly according to claim 17, wherein an overall length of the headgear assembly is in the range of 640-680 mm and an overall height of the headgear assembly is in the range of 175-215 mm.

27. The headgear assembly according to claim 26, wherein an overall length of the headgear assembly is 660 mm and an overall height of the headgear assembly is 196.1 mm.

28. The headgear assembly according to claim 17, wherein the pair of upper straps of the intermediate strap arrangement are angled with respect to the upper rear strap in the range of 40-50° and have a width in the range of 16-22 mm.

29. The headgear assembly according to claim 17, wherein the pair of upper straps of the intermediate strap arrangement are angled with respect to the upper rear strap at an angle of 45° and have a width of 19 mm.

30. The headgear assembly according to claim 17, wherein the intermediate strap arrangement interconnects the upper and lower rear straps.

31. The headgear assembly according to claim 17, wherein the at least two rear straps comprise generally flat, flexible composite material.

* * * * *